United States Patent [19]

Anderson

[11] Patent Number: 4,686,237
[45] Date of Patent: Aug. 11, 1987

[54] ERYTHRO-(E)-7-[3'-$C_{1-3}$ALKYL-1'-(3'',5''-DIMETHYLPHENYL)NAPHTH-2'-YL]-3,5-DIHYDROXYHEPT-6-ENOIC ACIDS AND DERIVATIVES THEREOF

[75] Inventor: Paul L. Anderson, Randolph, N.J.

[73] Assignee: Sandoz Pharmaceuticals Corp., E. Hanover, N.J.

[21] Appl. No.: 831,394

[22] Filed: Feb. 19, 1986

Related U.S. Application Data

[63] Continuation of Ser. No. 633,809, Jul. 24, 1984, abandoned.

[51] Int. Cl.[4] .................. C07D 309/30; C07C 69/618; A61K 31/365; A61K 31/225
[52] U.S. Cl. ..................... 514/532; 560/56; 562/466; 549/292; 514/557; 514/824
[58] Field of Search .............. 549/289, 274, 292, 291, 549/415, 417; 560/104, 56, 59, 119; 514/451, 532, 557; 562/501, 466

[56] References Cited

U.S. PATENT DOCUMENTS

| | | | |
|---|---|---|---|
| 3,983,140 | 9/1976 | Endo et al. | 260/343.5 |
| 4,198,425 | 4/1980 | Mitsui et al. | 424/279 |
| 4,248,889 | 2/1981 | Oka et al. | 424/308 |
| 4,255,444 | 3/1981 | Oka et al. | 424/279 |
| 4,308,378 | 12/1981 | Stokker | 542/441 |
| 4,351,844 | 9/1982 | Patchett et al. | 424/279 |
| 4,361,515 | 11/1982 | Terahara et al. | 549/292 |
| 4,375,475 | 3/1983 | Willard et al. | 424/279 |
| 4,376,863 | 3/1983 | Lam | 549/292 |
| 4,387,242 | 6/1983 | Lam | 560/119 |
| 4,440,927 | 4/1984 | Prugh | 549/292 |
| 4,474,971 | 10/1984 | Wareing | 549/214 |

FOREIGN PATENT DOCUMENTS 0895445  4/1983  Belgium .............. 549/292
0038061  10/1981  European Pat. Off. .

OTHER PUBLICATIONS

Derwent Abstracts 20213 D/12, JP 56-7775 (1/27/81) Sankyo KK.
Hulcher, Arch. Biochem. Biophys. 146, 422–427 (1971).
Sato et al., Chem. Pharm. Bull. 28, 1509–1525 (1980).
Singer et al., Proc. Soc. Exp. Biol. Med. 102, 370–373 (1959).

Primary Examiner—Glennon H. Hollrah
Assistant Examiner—Dara L. Dinner
Attorney, Agent, or Firm—Gerald D. Sharkin; Richard E. Vila; Melvyn M. Kassenoff

[57] ABSTRACT

Compounds of the formula

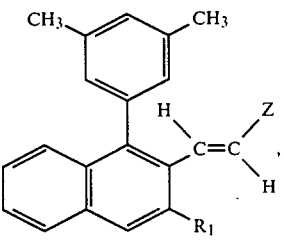

wherein
$R_1$ is $C_{1-3}$alkyl, and
Z is

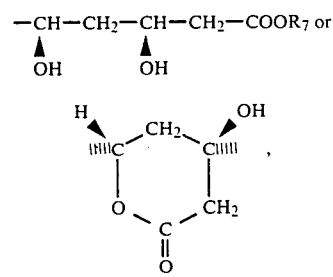

wherein $R_7$ is hydrogen, $R_8$ or M,
wherein
$R_8$ is a physiologically acceptable and hydrolyzable ester group, and
M is a pharmaceutically acceptable cation, the use thereof for inhibiting cholesterol biosynthesis and lowering the blood cholesterol level and, therefore, in the treatment of hyperlipoproteinemia and atherosclerosis, pharmaceutical compositions comprising such compounds and processes for and intermediates in the synthesis of such compounds.

15 Claims, No Drawings

ERYTHRO-(E)-7-[3'-C$_{1-3}$ALKYL-1'-(3",5"-DIMETHYLPHENYL)NAPHTH-2'-YL]-3,5-DIHYDROXYHEPT-6-ENOIC ACIDS AND DERIVATIVES THEREOF

This application is a continuation of application Ser. No. 633,809, filed July 24, 1984 and now abandoned.

This invention relates to compounds of the formula

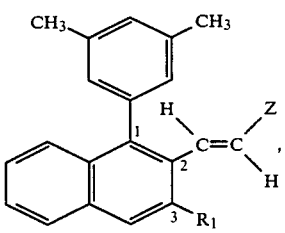

wherein
$R_1$ is C$_{1-3}$alkyl, and
Z is

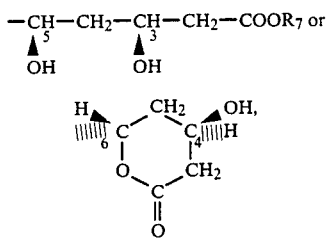

wherein $R_7$ is hydrogen, $R_8$ or M,
wherein
$R_8$ is a physiologically acceptable and hydrolyzable ester group, and
M is a pharmaceutically acceptable cation,
processes for and intermediates in the synthesis thereof, pharmaceutical compositions comprising a compound of Formula I and the use of the compounds of Formula I for inhibiting cholesterol biosynthesis and lowering the blood cholesterol level and, therefore, in the treatment of hyperlipoproteinemia and atherosclerosis.

By the term "physiologically acceptable and hydrolyzable ester group" is meant a group which, together with the —COO— radical to which it is attached, forms an ester group which is physiologically acceptable and hydrolyzable under physiological conditions to yield a compound of Formula I wherein $R_7$ is hydrogen and an alcohol which itself is physiologically acceptable, i.e., non-toxic at the desired dosage level, and which, preferably, is free of centers of asymmetry. Examples of such groups are C$_{1-3}$alkyl, n-butyl, i-butyl, t-butyl and benzyl, collectively referred to as $R_8'$.

As is self-evident to those in the art, each compound of Formula I (and every subscope and species thereof) has two centers of asymmetry (the two carbon atoms bearing the hydroxy groups in the group of Formula a and the carbon atom bearing the hydroxy group and the carbon atom having the free valence in the group of Formula b) and, therefore, there are two stereoisomeric forms (enantiomers) of each compound (a racemate), provided that $R_7$ does not contain any center of asymmetry. The two stereoisomers of the compounds wherein Z is a group of Formula a are the 3R,5S and 3S,5R isomers and the two stereoisomers of the compounds wherein Z is a group of Formula b are the 4R,6S and 4S,6R isomers, both the individual stereoisomers and the racemates being within the scope of this invention. When $R_7$ contains one or more centers of asymmetry, there are four or more stereoisomers. Since it is preferred that $R_7$ not contain a center of asymmetry and for reasons of simplicity any additional stereoisomers resulting from the presence of one or more centers of asymmetry in $R_7$ will be ignored, it being assumed that $R_7$ is free of centers of asymmetry.

The preferred stereoisomer of each compound wherein Z is a group of Formula a is the 3R,5S isomer and the preferred stereoisomer of each compound wherein Z is a group of Formula b is the 4R,6S isomer. These preferences also apply to the compounds of Formula I having more than two centers of asymmetry and represent the preferred configurations of the indicated positions.

$R_1$ is preferably methyl or isopropyl.

$R_7$ is preferably $R_7'$, where $R_7'$ is hydrogen, C$_{1-3}$alkyl or M, more preferably $R_7''$, where $R_7''$ is hydrogen, C$_{1-2}$alkyl or M, and most preferably M, especially sodium. M is preferably M' and most preferably sodium.

$R_8$ is preferably $R_8'$, where $R_8'$ is C$_{1-3}$alkyl, n-butyl, i-butyl, t-butyl or benzyl, more preferably C$_{1-3}$alkyl and most preferably C$_{1-2}$alkyl.

M is preferably free from centers of asymmetry and is more preferably M', i.e., sodium, potassium or ammonium, and most preferably sodium. For simplicity, each of the formulae in which M appears (in the specification and the claims) has been written as if M were monovalent and, preferably, it is. However, it may also be divalent or trivalent and, when it is, it balances the charge of two or three carboxy groups, respectively.

The preferred compounds of Formula I wherein Z is a group of Formula a are those
(i) wherein $R_7$ is $R_7'$,
(ii) of (i) wherein $R_7$ is $R_7''$,
(iii) of (ii) wherein $R_7$ is M,
(iv) of (iii) wherein $R_7$ is M',
(v) of (iv) wherein $R_7$ is sodium, and
(vi)–(x) of (i)–(v) wherein $R_1$ is methyl or isopropyl.

Groups (i)–(x) embrace the 3R,5S-3S,5R racemates and the 3R,5S and 3S,5R enantiomers, of which the racemates and the 3R,5S enantiomers are preferred.

The preferred compounds of Formula I wherein Z is a group of Formula b are those wherein $R_1$ is methyl or isopropyl. This group embraces the 4R,6S-4S,6R racemates and the R,6S and 4S,6R enantiomers, of which the racemates and the R,6S enantiomers are preferred.

The compounds of Formula I wherein $R_1$ is methyl, and Z is a group of Formula a wherein $R_7$ is hydrogen, ethyl or or a group of Formula b are synthesized as set forth in Examples 1–5.

The compounds of Formula I wherein $R_1$ is ethyl, and Z is a group of Formula a wherein $R_7$ is hydrogen, ethyl or sodium or a group of Formula b may be synthesized by the processes of Examples 1–5 with the following additional step: The compound of Formula CCXLII is converted to the corresponding compound having an ethyl group in the 3-position of the naphthalene ring by the procedure utilized to convert the compound of Formula CCXLI to the compound of Formula CCXLII, i.e., the procedure of Step 8 of Example 1. Otherwise, the synthesis is the same.

The compounds of Formula I wherein $R_1$ is isopropyl, and Z is a group of Formula a wherein $R_7$ is hydrogen, ethyl or sodium or a group of Formula b may be synthesized by the processes of Example A, Steps 9-13 of Example 1 and Examples 2-5. The corresponding compounds of Formula I wherein $R_1$ is n-$C_{1-3}$alkyl may be synthesized analogously utilizing in Step 8 of Example A the corresponding n-$C_{1-3}$alkylmagnesium chloride or bromide in lieu of isopropylmagnesium chloride.

The compounds of Formula I wherein Z is a group of Formula a wherein $R_7$ is any other significance of $R_8'$ may be synthesized by the processes of the preceding three paragraphs utilizing appropriate starting materials.

The compounds of Formula I wherein Z is a group of Formula a wherein $R_7$ is $R_8$ may be synthesized by reacting the corresponding compound wherein Z is a group of Formula b with at least 2, e.g., 2-10, preferably 2.05-2.5, moles of a compound of the formula $M_2\oplus\ominus OR_8$, wherein $M_2$ is sodium or potassium, per mole of the compound wherein Z is a group of Formula b, at 0°-70° C., preferably 20°-50° C., for 2-12 hours, in an inert organic solvent, preferably an inert ether solvent such as tetrahydrofuran or, if the corresponding alcohol of the formula $R_8$—OH is a liquid at the desired reaction temperature, preferably said corresponding alcohol. By the term "corresponding alcohol" is meant that $R_8$ in the compound of the formula $M_2\oplus\ominus OR_8$ and in the alcohol of the formula $R_8$—OH is the same. The compounds of Formula I wherein Z is a group of Formula a wherein $R_7$ is $R_8$ may also be prepared by esterifying the corresponding compound wherein $R_7$ is hydrogen with an alcohol of the formula $R_8$—OH. Conveniently, the compound wherein $R_7$ is hydrogen is treated with a large excess of the alcohol of the formula $R_8$—OH (e.g., 2-50 moles per mole of the compound wherein $R_7$ is hydrogen) at 20°-40° C. for 2-12 hours in the presence of a catalytic amount of an acid such as p-toluenesulfonic acid. The excess alcohol serves as the solvent. The reaction may also be run in an inert organic solvent, e.g., an ether such as tetrahydrofuran, and must be run in such a solvent if the alcohol of the formula $R_8$—OH is not a liquid at the desired reaction temperature.

The compounds of Formula I wherein Z is a group of Formula a wherein $R_7$ is M may be synthesized by neutralizing the corresponding compounds wherein $R_7$ is hydrogen with 0.95-1, preferably 0.96-0.99, equivalent of a base of the formula $M\oplus\ominus OH$ per mole of the compound wherein $R_7$ is hydrogen at 0°-25° C., preferably 20°-25° C., for 1-10 minutes, in an inert aqueous organic solvent, for example a mixture of water and a $C_{1-2}$alkanol. As should be evident from what is set forth above, the formula $M\oplus\ominus OH$ embraces bases of the formulae $M\oplus^2(\ominus OH)_2$ and $M\ominus^3(\ominus OH)_3$.

The processes described above yield racemates. However, techniques for separating a racemate into its two optically active enantiomers are known. For example, a racemic compound having a carboxylic acid group may be reacted with an optically pure organic base having at least one center of asymmetry to form a mixture of diastereoisomeric salts or amides that may be separated by fractional crystallization, column chromatography, preparative thin layer chromatography, high pressure liquid chromatography, etc. or it may be reacted with an optically pure alcohol having at least one center of asymmetry to form a mixture of diastereoisomeric esters which may be separated by conventional techniques such as those set forth above. On the other hand, a racemic compound having a hydroxy group, for example a compound of Formula I wherein Z is a group of Formula b, may be esterified with an optically pure carboxylic acid having at least one center of asymmetry to form a mixture of diastereoisomeric esters or it may be reacted with an optically pure trisubstituted silyl halide having an asymmetric silicon atom, for example (−)-α-naphthylphenylmethylchlorosilane (Sommer et al., J. Am. Chem. Soc. 80, 3271 (1958).), to form a mixture of two diastereoisomeric silyloxy compounds, which mixture may be separated by conventional techniques. After separation, the optically pure salts, amides, esters or silyloxy compounds are reconverted to the corresponding carboxy group- or hydroxy group-containing compounds with retention of optical purity. For example, (−)-α-naphthylphenylmethylsilyl and other silyl groups may be cleaved with a fluoride reagent, for example, tetra-n-butylammonium fluoride in an anhydrous inert organic medium containing glacial acetic acid, preferably tetrahydrofuran containing 1-2 moles, preferably 1.2-1.5 moles, of glacial acetic acid per mole of the fluoride compound. The reaction temperature is suitably 20°-60° C., preferably 20°-30° C., and the reaction time is suitably 8-24 hours, particularly when the reaction temperature is 20°-30° C. Approximately 1-5 moles, preferably 2-4 moles, of fluoride reagent per mole of the silyl group-containing compound are utilized. The reaction mixture should be acidic at the time the fluoride reagent is added to maximize production of the desired product.

Most of the processes described above are described in greater detail in my application Ser. No. 06/570,584, filed Jan. 13, 1984 and now abandoned and titled Naphthalene And Tetrahydronaphthalene Derivatives Of Mevalonolactone and Derivatives Thereof. Where the reaction conditions set forth in said application differ from those set forth herein, the reaction conditions set forth in said application may also be utilized for the compounds of this specification. Said application, particularly pages 15-67, 109-118 and 125-151, is hereby incorporated by reference.

Also described in said application Ser. No. 06/570,584 are processes by which the 4R,6S isomers of the compounds of Formula I wherein Z is a group of Formula b and the 3R,5S isomers of the compounds of Formula I wherein Z is a group of Formula a may be synthesized.

All of the reagents and reactants the synthesis of which is not described in this specification are either known or are synthesizable by processes analogous to those described in the literature for similar known compounds.

The product of each reaction may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure liquid chromatography. Often, however, the crude product of one reaction may be employed in the following reaction without purification.

Since any compound of Formula I wherein Z is a group of Formula a wherein $R_7$ is a cation other than M may be converted into the corresponding compounds wherein $R_7$ is hydrogen, M or $R_8$ by acidification optionally followed by neutralization or esterification, ion exchange, etc., the compounds of Formula I wherein Z is a group of Formula a and $R_7$ is a pharmaceutically unacceptable cation are also within the scope of this invention inasmuch as they are useful as intermediates. However, such compounds are not compounds of Formula I as utilized in this specification, except where indicated to the contrary.

Besides having the utility set forth below, every compound of Formula I is useful as an intermediate in the synthesis of one or more other compounds of Formula I utilizing the reactions set forth in this specification, e.g., those of Examples 2–5.

Also within the scope of this invention are the intermediates of Formulae CCXLI–CCXLVI and the compounds corresponding to those of Formulae CCXLII–CCXLVI but having a $C_{2-3}$alkyl group in the 3-position of the naphthalene ring in lieu of the methyl group and those corresponding to that of Formula CCXLVI but having, in lieu of the ethyl group, a different significance of $R_8'$ and, optionally, in lieu of the methyl group in the 3-position of the naphthalene ring, a $C_{2-3}$alkyl group.

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates, and, therefore, as hypolipoproteinemic and antiatherosclerotic agents. The biological activity of the compounds of Formula I may be demonstrated in the following three tests:

Test A. In Vitro Microsomal Assay of HMG-CoA Reductase Inhibition:

200 μl. aliquots (1.08–1.50 mg./ml.) of rat liver microsomal suspensions, freshly prepared from male Sprague-Dawley rats (150–225 g. body weight), in Buffer A with 10 mmol. dithiothreitol are incubated with 10 μl. of a solution of the test substance in dimethylacetamide and assayed for HMG-CoA reductase activity as described in Ackerman et al., J. Lipid Res. 18, 408–413 (1977). In the assay the microsomes are the source of the HMG-CoA reductase enzyme which catalyzes the reduction of HMG-CoA to mevalonate. The assay employs a chloroform extraction to separate the product, [$^{14}$C]mevalonolactone, formed by the HMG-CoA reductase reaction from the substrate, [$^{14}$C]HMG-CoA. [$^{3}$H]mevalonolactone is added as an internal reference. Inhibition of HMG-CoA reductase is calculated from the decrease in specific activity ([$^{14}$C/$^{3}$H]mevalonate) of test groups compared to controls.

Test B. In Vitro Cell Culture Cholesterol Biosynthesis Screen:

The cell culture is prepared as follows: Stock monolayer cultures of the Fu5AH rat hepatoma cell line (originally obtained from G. Rothblat; see Rothblat, Lipids 9, 526–535 (1974)) are routinely maintained in Eagle's Minimum Essential Medium (EMEM) supplemented with 10% fetal bovine serum (FBS) in 75 cm.$^2$ tissue culture flasks. For these studies, when the cultures reach confluence, they are removed by mild enzymatic treatment with 0.25% trypsin in Hanks' balanced salt solution (without calcium and magnesium). After centrifugation of the cell suspension and aspiration of the enzymatic solution, the cell pellet is resuspended in an appropriate volume of media for seeding into 60 mm. tissue culture dishes. The cultures are incubated at 37° C. in an atmosphere of high humidity and 5% carbon dioxide. When the cultures are confluent (approximately 5 days), they are ready for use. The culture media is aspirated from the dishes and replaced with 3 ml. of EMEM supplemented with 5 mg./ml. of delipidized serum protein (DLSP) prepared by the method of Rothblat et al., In Vitro 12, 554–557 (1976). Replacement of the FBS with DLSP has been shown to stimulate the incorporation of [$^{14}$C]acetate into sterol by removing the exogenous sterol supplied by the FBS, thereby requiring the cells to synthesize sterol. Enhanced 3=hydroxy-3-methylglutaryl Coenzyme A reductase (HMG-CoA reductase) actiVity is measurable in the cells in response to the lack of exogenous sterol. Following approximately 24 hours incubation at 37° C. in the DLSP supplemented media, the assay is initiated by the addition of 3μCi of [$^{14}$C]acetate and the test substance solubilized in dimethylsulfoxide (DMSO) or distilled water. Solvent controls and compactin-treated controls are always prepared. Triplicate 60 mm. tissue culture dishes are run for each group. After 3 hours incubation at 37° C., the cultures are examined microscopically using an inverted phase contrast microscope. Notations are made of any morphological changes which may have occurred in the cultures. The media is aspirated and the cell layer is gently washed twice with 0.9% sodium chloride solution (saline). The cell layer is then harvested in 3 ml. of 0.9% saline by gentle scraping with a rubber policeman and transferred to a clean glass tube with Teflon lined cap. The dishes are rinsed with 3 ml. of 0.9% saline and rescraped, and the cells are combined with the first harvest. The tubes are centrifuged at 1500 r.p.m. for 10 minutes in an IEC PR-J centrifuge, and the supernatant is aspirated.

The cells are then extracted as follows: One ml. of 100% ethanol is added to the cell pellet followed by sonication for 10 seconds with a "LO" setting of 50 on a Bronwell Biosonik IV. One hundred 1. are taken for protein determination. One ml. of 15% potassium hydroxide (KOH) is added, and the samples are thoroughly vortexed. Saponification is accomplished by heating the ethanol-KOH treated samples at 60° C., for 60 minutes in a water bath. Following dilution of the samples with 2 ml. of distilled water, they are extracted three times with 7 ml. of petroleum ether. The petroleum ether extracts are then washed three times with 2 ml. of distilled water and finally taken to dryness under a stream of nitrogen.

The obtained samples are then analyzed by thin layer chromatography (TLC) as follows: Residues from the petroleum ether extraction are taken up in a small volume of hexane and spotted on silica gel 60 TLC plates (E. Merck). Development of the plates is carried out in a three phase solvent system consisting of 150 parts by volume hexane: 50 parts by volume diethyl ether: 5 parts by volume glacial acetic acid. Visualization is accomplished in an iodine vapor chamber. The plates are divided into five sections such that each section contains the molecules having the following approximate Rf values: section 1—0–0.4, section 2—0.4–0.55, section 3—0.55–0.7, section 4—0.7–0.9 and section 5—0.9–1.0. Section 2 contains the non-saponifiable sterols. The five sections of the TLC plates are scraped into scintillation vials. Blanks are also prepared from scrapings of chromatographed non-labelled standards. ACS ® scintillation cocktail is added, and the radioactivity is determined in a liquid scintillation spectrometer. [$^{14}$C]hexadecane standards are used to determine counting efficiencies. The total protein content of the samples is determined employing the Bio-Rad Protein Assay System.

The results are reported as disintegrations per minute per mg. protein (d.p.m./mg. protein) for each of the five TLC sections. Mean d.p.m./mg. protein ± standard error of the mean are calculated, and drug treated means are compared for percentage change (%Δ) and statistical significance with solvent control means. TLC section 2 data is taken as a measure of HMG-CoA reductase activity inhibition.

Test C: In Vivo Cholesterol Biosynthesis Inhibition Test: In vivo studies utilize male Wistar Royal Hart rats weighing 150±20 g. which have been kept for 7-10 days on an altered light cycle (6:30 A.M.-6:30 P.M. dark) housed two per cage and fed powdered Purina Rat Chow and water ad libitum. Three hours before the diurnal maximum of cholesterol synthesis at mid-dark, the rats are administered the test substance dissolved or as a suspension in 0.5% carboxymethylcellulose in a volume of 1 ml./100 g. body weight. Controls receive vehicle alone. One hour after receiving the test substance, the rats are injected intraperitoneally with about 25 μCi/100 g. body weight of sodium [1-$^{14}$C]acetate 1-3 mCi/mmol. Two hours after mid-dark, blood samples are obtained under sodium hexobarbitol anesthesia and the serum is separated by centrifugation.

Serum samples are saponified and neutralized, and the 3β-hydroxysterols are precipitated with digitonin basically as described in Sperry et al., J. Biol. Chem. 187, 97 (1950). The [$^{14}$C]digitonides are then counted by liquid scintillation spectrometry. After correcting for efficiencies, the results are calculated in nCi (nanocuries) of sterol formed per 100 ml. of serum. Inhibition of sterol synthesis is calculated from the reduction in the nCi of sterols formed from test groups compared to controls.

The following results were obtained:

| Test A: | Example 1 | $IC_{50}$ = 0.08 μmolar |
| --- | --- | --- |
| | Example 2 | $IC_{50}$ = 0.01 μmolar |
| | Example 4 | $IC_{50}$ = 0.33 μmolar |
| | Compactin | $IC_{50}$ = 0.77 μmolar |
| | Mevinolin | $IC_{50}$ = 0.14 μmolar |
| | \multicolumn{2}{l}{$IC_{50}$ is the concentration of the test substance in the assay system calculated to produce a 50% inhibition of HMG-CoA reductase activity.} |
| Test C: | Example 1 | −35% at 0.5 mg./kg. |
| | Example 2 | $ED_{50}$ = 0.3 mg./kg. |
| | Example 4 | −20% at 0.5 mg./kg. |
| | Compactin | $ED_{50}$ = 3.5 mg./kg. |
| | Mevinolin | $ED_{50}$ = 0.41 mg./kg. |

As set forth above, the compounds of Formula I (including each and every subgroup thereof set forth in the specification and/or the claims) inhibit cholesterol biosynthesis and are useful for lowering the blood cholesterol level in animals, particularly mammals and more particularly larger primates, and, therefore, as hypolipoproteinemic and antiatherosclerotic agents.

The compounds of Formula I may be formulated into conventional pharmaceutical compositions and administered by conventional modes of administration. The compounds of each and every subgroup thereof in the specification and/or claims may likewise be formulated into conventional pharmaceutical compositions.

The compounds of Formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means. The preferred pharmaceutical compositions from the standpoint of ease of preparation and administration are solid compositions, particularly tablets and capsules.

The precise dosage of the compound of Formula I to be employed for inhibiting cholesterol biosynthesis depends upon several factors including the host, the nature and the severity of the condition being treated, the mode of administration and the particular compound employed. However, in general, satisfactory inhibition or reduction of cholesterol biosynthesis (i.e., satisfactory reduction of the blood cholesterol level and satisfactory treatment of hyperlipoproteinemia and atherosclerosis) is achieved when a compound of Formula I is administered orally at a daily dosage of 0.01-100 mg./kg. body weight, e.g., 0.01-20 mg./kg. body weight for the compound of Example 2, or, for most larger primates, a daily dosage of 1-1000 mg. and suitably 1-150 mg., e.g., 5-100 mg., for the compound of Example 2.

The daily dosage is usually divided into two to four equal portions or administered in sustained release form. Usually, a small dosage is administered initially, and the dosage is gradually increased until the optimal dosage for the host under treatment is determined. For administration by injection, a dosage somewhat lower than would be used for oral administration of the same compound to the same host having the same condition is usually employed. However, the above dosages are also typically used for i.v. administration.

A typical dosage unit for oral administration may contain 0.5-500 mg. of a compound of Formula I. Preferred dosage units contain 0.5 to 75 mg. of a compound of Formula I, for example, 1-50 mg. of the compound of Example 2.

The compounds of Formula I (including those of each and every subgroup thereof) may be formulated into such pharmaceutical compositions containing an amount of the active substance that is effective for inhibiting cholesterol biosynthesis, such compositions in unit dosage form and such compositions comprising a solid pharmaceutically acceptable carrier.

A representative formulation prepared by conventional techniques for encapsulation in a hard gelatin capsule is:

| | |
| --- | --- |
| Compound of Formula I, e.g., the compound of Example 2 | 25 mg. |
| Corn starch | 224 mg. |
| Magnesium stearate | 1 mg. |

A representative formulation suitable for preparing tablets by conventional means is:

| | |
| --- | --- |
| Compound of Formula I, e.g., the compound of Example 2 | 10 mg. |
| Polyvinylpyrrolidone USP | 5 mg. |
| Powdered lactose | 124 mg. |
| Corn starch | 10 mg. |
| Magnesium stearate | 1 mg. |

The following examples show representative compounds encompassed by this invention and their synthesis. However, it should be understood that they are for purposes of illustration only.

EXAMPLE 1

Ethyl erythro-(E)-3,5-dihydroxy-7-[1'-(3'',5''-dimethylphenyl)-3-methylnaphth-2'-yl]hept-6-enoate

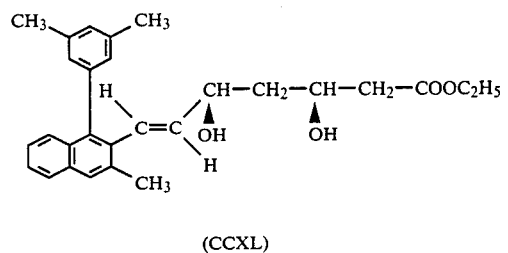
(CCXL)

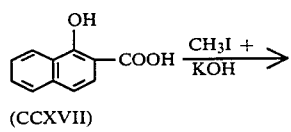
(CCXVII)

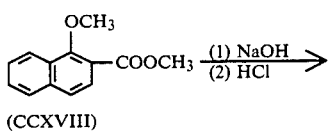
(CCXVIII)

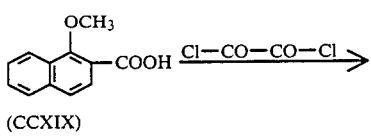
(CCXIX)

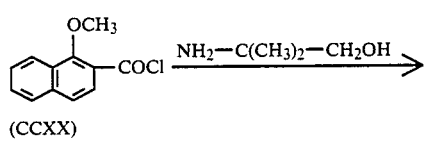
(CCXX)

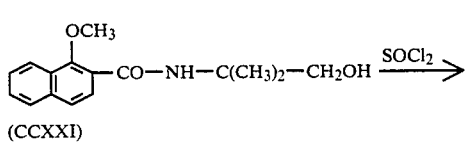
(CCXXI)

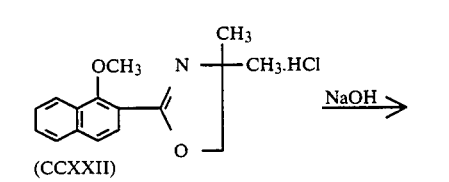
(CCXXII)

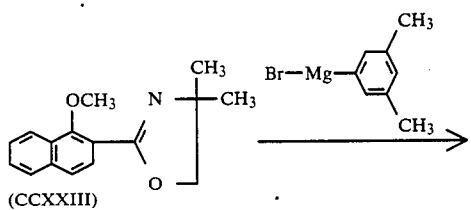
(CCXXIII)

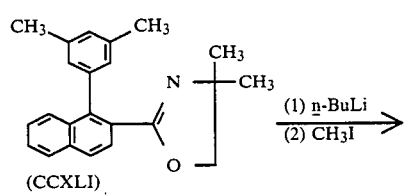
(CCXLI)

-continued

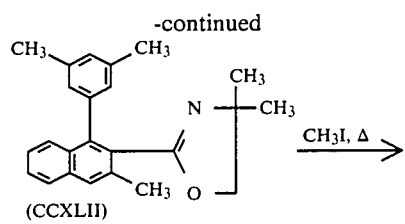
(CCXLII)

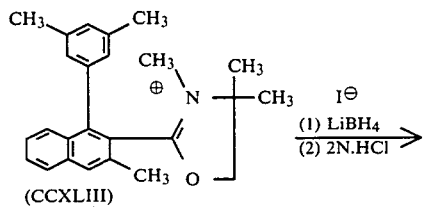
(CCXLIII)

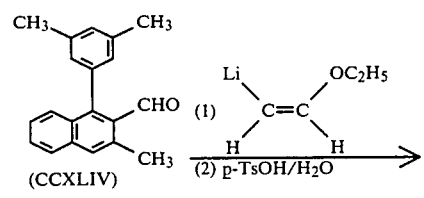
(CCXLIV)

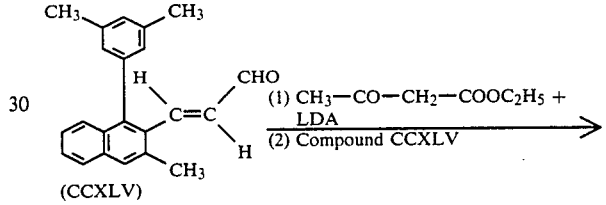
(CCXLV)

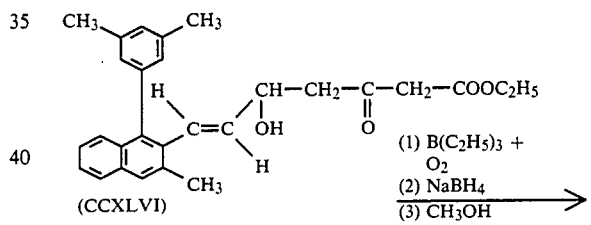
(CCXLVI)

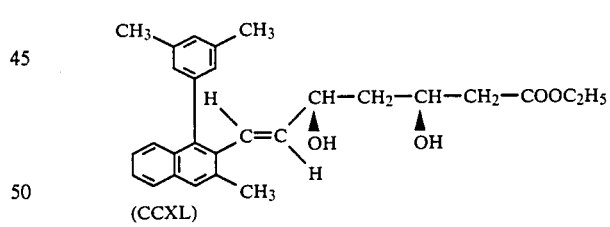
(CCXL)

Step 1

Methyl 1-methoxy-2-naphthoate (Compound CCXVIII)

Over a 15 minute period, 149 g. (2.7 moles) of ground potassium hydroxide is added to 180 g. (0.96 mole) of 1-hydroxy-2-naphthoic acid in 2.5 l. of dimethylformamide (during the course of which the temperature rises to 32° C.). The reaction mixture is stirred at 20°–25° C. for 16 hours and at 50° C. for 2 hours and cooled to 40° C. 387 g. (2.7 moles) of methyl iodide is added, and the reaction mixture is stirred at 40°–50° C. for 4 hours. 4 l. of saturated sodium chloride solution is added, and the mixture is extracted with diethyl ether. The diethyl ether extract is dried over anhydrous sodium sulfate and evaporated at reduced pressure to obtain the crude product as a light brown oil (255 g.).

Step 2

1-Methoxy-2-naphthoic acid (Compound CCXIX)

Over a 15-20 minute period, 750 ml. of 2N. sodium hydroxide (1.5 moles) is added to 255 g. (≦0.96 mole) of crude Compound CCXVIII in 2.5 l. of methanol stirred at 20°-25° C., and the reaction mixture is stirred at 20°-25° C. for 16 hours. 5 l. of water is added, and the mixture is extracted with diethyl ether (to recover any unreacted starting material). The aqueous phase is acidified with 2N. hydrochloric acid and extracted with methylene chloride. The methylene chloride extract is dried over anhydrous sodium sulfate and evaporated at reduced pressure, and the residue is crystallized from ethyl acetate/petroleum ether. The solids are collected by filtration, washed with petroleum ether and vacuum dried at 40° C. to obtain the white crystalline product (164 g. (84% Steps 1 and 2 combined)), m.p. 124°-127° C.

Step 3

1-Methoxy-2-naphthoyl chloride (Compound CCXX)

Over a 30 minute period, 201 g. (1.58 moles) of oxalyl chloride is added to 160 g. (0.79 mole) of Compound CCXIX in 1 l. of dry toluene stirred at 60° C. under nitrogen. (Compound CCXIX slowly dissolves with moderate foaming during the addition.) The reaction mixture is refluxed for 2 hours under nitrogen and concentrated to a volume of 600 ml. using a Dean-Stark trap. 300 ml. of dry toluene is added in small portions while the volume is gradually reduced. The reaction mixture is evaporated to dryness at reduced pressure to obtain the crude product.

Step 4

1-Methoxy-2-naphthoic acid N-1,1-dimethyl-2-hydroxyethylamide (Compound CCXXI)

The crude product of Step 3 in 300 ml. of dry methylene chloride is added, over a 1 hour period, to 239.9 g. (1.89 moles) of 2-amino-2-methyl-1-propanol in 1.5 l. of methylene chloride stirred at 0°-10° C. under nitrogen. The reaction mixture is allowed to warm to 20°-25° C. and is stirred at this temperature for 16 hours, the reaction mixture being maintained under nitrogen throughout. Water is added, and the mixture is extracted with methylene chloride. The methylene chloride extract is washed with 2N. hydrochloric acid, washed with 10% sodium bicarbonate solution, dried over anhydrous sodium sulfate and evaporated at reduced pressure, and the residue is crystallized from diethyl ether/petroleum ether. The solids are collected by filtration, washed with petroleum ether and vacuum dried at 40° C. to obtain the product as a white solid (206.7 g. (95.8% Steps 3 and 4 combined)), m.p. 92°-95° C. An analytical sample melted at 95°-97° C.

Step 5

4,4-Dimethyl-2-(1'-methoxynaphth-2'-yl)-2-oxazoline . hydrochloride (Compound CCXXII)

Over a 30 minute period, 180 ml. (2.47 moles) of thionyl chloride is added to 206 g. (0.75 mole) of Compound CCXXI in 300 ml. of dry methylene chloride stirred at 20° C. under nitrogen with cooling, and the reaction mixture is stirred at 20°-25° C. under nitrogen for 2 hours. The volume of the reaction mixture is reduced by about 50% at reduced pressure, and 1.4 l. of diethyl ether is added while cooling (at 0°-10° C.) and rapidly agitating the mixture. The mixture is stirred at 0°-10° C. for 1.5 hours, and the precipitate is collected by filtration, washed with diethyl ether and air dried to obtain the crude product as a white solid (248.1 g.).

Step 6

4,4-Dimethyl-2-(1'-methoxynaphth-2'-yl)-2-oxazoline (Compound CCXXIII)

1 l. of ethyl acetate is added to 248 g. of crude Compound CCXXII in 1.5 l. of water, and, with rapid agitation, the mixture is made strongly basic with 2N. sodium hydroxide solution. The ethyl acetate phase is separated, and the aqueous phase is extracted twice with ethyl acetate. The three ethyl acetate phases are combined, dried over anhydrous sodium sulfate and evaporated at reduced pressure to a small volume. Petroleum ether is slowly added while cooling the mixture, and the resulting precipitate is collected by filtration and washed with petroleum ether to obtain the product as a light tan crystalline solid (167.7 g. (87.2% Steps 5 and 6 combined)), m.p. 73°-77° C.

Step 7

4,4-Dimethyl-2-[1'-(3",5"-dimethylphenyl)naphth-2'-yl]-2-oxazoline (Compound CCXLI)

(a) Preparation of Grignard reagent: 80 g. (0.432 mole) of 1-bromo-3,5-dimethylbenzene is added over a 1 hour period to 10.8 g. (0.44 mole) of magnesium turnings and a trace of iodine in 545 ml. of dry tetrahydrofuran (distilled over sodium) stirred under nitrogen, the addition being at a rate such that the reaction mixture gently refluxes, the reaction mixture being heated at 40°-45° C. to initiate the reaction. After the reaction, the reaction mixture is refluxed for 2 hours under nitrogen and cooled to 20°-25° C.

(b) The Grignard reagent solution from Part (a) of this step is slowly added over a 45 minute period to 84.0 g. (0.329 mole) of Compound CCXXIII stirred at 45° C. in 500 ml. of dry tetrahydrofuran under nitrogen with cooling (the reaction being exothermic). The reaction mixture is stirred at 20°-25° C. under nitrogen for 16 hours and is quenched by addition of saturated ammonium chloride solution. The mixture is extracted with ethyl acetate, and the ethyl acetate extract is dried over anhydrous sodium sulfate and evaporated at reduced pressure to a small volume. While cooling and agitating the mixture, diethyl ether and then petroleum ether are added. The resulting solids are collected by filtration and vacuum dried at 40° C. to obtain the white crystalline product (57.0 g.), m.p. 97°-100° C. A second crop (15.8 g.) and a third crop are also obtained.

Step 8

4,4-Dimethyl-2-[1'-(3",5"-dimethylphenyl)-3'-methylnaphth-2'-yl]-2-oxazoline (Compound CCXLII)

Over a 30 minute period, 236.1 ml. of 1.6M. n-butyllithium/n-hexane (0.377 mole) is added to 108 g. (0.33 mole) of Compound CCXLI in 1.8 l. of anhydrous diethyl ether stirred at −5° C., the reaction mixture is stirred at −5° C. for 1 hour, 85.8 g. (0.60 mole) of methyl iodide is added dropwise over a 15 minute period with stirring at −5° C., and the reaction mixture is allowed to warm to 20°-25° C. and stirred at 20°-25° C.

for 16 hours, the reaction mixture being maintained under nitrogen throughout. The reaction mixture is carefully poured into a mixture of saturated sodium chloride solution and ice and filtered to remove some insoluble material. The diethyl ether phase is separated, the aqueous phase is extracted with diethyl ether, and the diethyl ether phases are combined, dried over anhydrous sodium sulfate and evaporated at reduced pressure to a small volume. Petroleum ether is added, and the crystalline product is collected and vacuum dried (89.5 g. (79%)), m.p. 153°–156° C.

Step 9

2-[1'-(3'',5''-Dimethylphenyl)-3'-methylnaphth-2'-yl]-3,4,4-trimethyl-2-oxazolinium iodide (Compound CCXLIII)

220 ml. (3.53 moles) of methyl iodide is added to 129 g. (0.376 mole) of Compound CCXLII in 600 ml. of nitromethane, and the reaction mixture is heated to 60° C. under nitrogen, stirred at 60° C. under nitrogen for 1 hour and cooled to 30.C during which the product begins to crystallize. 1 l. of diethyl ether is added at 30° C., the mixture is stirred for 15–20 minutes, and the solids are collected by filtration, washed with diethyl ether and vacuum dried at 45° C. to obtain the crystalline product (171 g. (93.7%), m.p.>290° C. (dec.)

Step 10

1-(3',5'-Dimethylphenyl)-3-methyl-2-naphthaldehyde (Compound CCXLIV)

(a) 37 g. (1.7 moles) of lithium borohydride is added portionwise over a 3 hour period to 150 g. (0.3 mole) of Compound CCXLIII in 1.8 l. of dry tetrahydrofuran (dried over molecular sieves) and 720 ml. of absolute ethanol (dried over molecular sieves) stirred at −15°−−5° C. under nitrogen. The reaction mixture is stirred for 2 hours at −10° C. under nitrogen, and a mixture of ice and saturated sodium chloride solution is added. The mixture is extracted with ethyl acetate, the ethyl acetate extract is dried over anhydrous sodium sulfate and evaporated at reduced pressure to a small volume, and the crystalline oxazolidine is obtained by the addition of diethyl ether followed by petroleum ether (94.1 g.), m.p. 151°–156° C. A second crop (5.7 g.) is also obtained.

(b) 1.5 l. of 2N. hydrochloric acid (3 moles) i.s added dropwise over a 15 minute period to 99 g. (0.275 mole) of the product of Part (a) of this step in 1.8 l. of ethanol and 600 ml. of tetrahydrofuran stirred at 15° C., and the reaction mixture is stirred at 20°–25° C. for 4 hours. Water is added, and the mixture is extracted with diethyl ether. The diethyl ether extract is dried over anhydrous sodium sulfate and evaporated to dryness at reduced pressure, and the residue is triturated with petroleum ether to obtain the product which is dried at 20°–25° C. under high vacuum (40 g.), m.p. 105°–107° C. A second crop (2.3 g.) is also obtained and additional product (7.4 g.) is obtained from the filtrate

Step 11

(E)-3-[1'-(3'',5''-Dimethylphenyl)-3'-methylnaphth-2'-yl]prop-2-enal (Compound CCXLV)

(a) Preparation of cis-1-ethoxy-2-tri-n-butylstannylethylene: 7.0 g. (0.1 mole) of ethoxyacetylene is added over a period of 1 hour to 29.1 g. (0.1 mole) of tri-n-butyltin hydride stirred under nitrogen at 50° C., and the reaction mixture is heated under nitrogen at 50°–55° C. for 3 hours and at 60°–70° C. for 1 hour.

(b) Preparation of cis-1-lithium-2-ethoxyethylene: 50.14 ml. of 1.6M. n-butyllithium/n-hexane (0.082 mole) is added dropwise over a 15 minute period to 28.9 g. (0.08 mole) of cis-1-ethoxy-2-tri-n-butylstannylethylene in 700 ml. of dry tetrahydrofuran stirred at −60° C. under nitrogen, and the reaction mixture is stirred at −60° C. under nitrogen for 1 hour to obtain a solution of cis-1-lithium-2-ethoxyethylene.

(c) 20.0 g. (0.073 mole) of Compound CCXLIV in 80 ml. of dry tetrahydrofuran is added to the product of Part (b) of this step, and the reaction mixture is stirred at −60° C. under nitrogen for 2 hours and carefully quenched with saturated ammonium chloride solution. (The temperature rises to 20°–25° C. during the addition.) The mixture is extracted with ethyl acetate, and the ethyl acetate extract is dried over anhydrous sodium sulfate and evaporated to dryness at reduced pressure. The residue is partitioned between acetonitrile and n-hexane, and the acetonitrile layer is reextracted with n-hexane and evaporated to dryness at reduced pressure to obtain the crude enol ether intermediate (19.9 g.).

(d) 400 ml. of tetrahydrofuran, 100 ml. of water and 1 g. of p-toluenesulfonic acid·H$_2$O are added to 10 g. of the enol ether product of Part (c) of this step, and the reaction mixture is stirred at 20°–25° C. for 16 hours. 1.5 l. of water is added, and the mixture is extracted three times with ethyl acetate. The ethyl acetate extracts are combined, washed with saturated sodium chloride solution, washed with 50–60 ml. of 10% sodium bicarbonate solution, washed with saturated sodium chloride solution, dried over anhydrous sodium sulfate and evaporated at reduced pressure. The residue is dried at 40° C. under high vacuum for 5 hours to obtain the crude product as a yellow oil (12.8 g.).

Step 12

Ethyl (E)-7-[1'-(3'',5''-dimethylphenyl)-3'-methylnaphth-2'-yl]-5-hydroxy-3-oxohept-6-enoate (Compound CCXLVI)

(a) 82.9 ml. of 1.6M. n-butyllithium/n-hexane (0.133 mole) is added dropwise to 13.4 g. (0.133 mole) of diisopropylamine in 360 ml. of dry tetrahydrofuran stirred at −5° C. under nitrogen, and the reaction mixture is stirred under the same conditions for 15 minutes to obtain a solution of lithium diisopropylamide.

(b) 8.6 g. (0.066 mole) of ethyl acetoacetate is added dropwise to the product of Part (a) of this step stirred at −5°–0° C., the reaction mixture is stirred at −5–0° C. for 1 hour and cooled to −60° C., a solution of 12 g. of crude Compound CCXLV (Step 11, Part (d)) in 100 ml. of dry tetrahydrofuran is slowly added, and the reaction mixture is stirred at −60° C. for 2 hours, the reaction mixture being maintained under nitrogen throughout. The reaction mixture is slowly added to saturated ammonium chloride solution, and the mixture is extracted with ethyl acetate. The ethyl acetate extract is dried over anhydrous sodium sulfate and evaporated to dryness at reduced pressure to obtain the crude product as an oil (12.8 g.).

The product is a racemate that may be resolved to obtain the 5R and 5S enantiomers.

Step 13

Ethyl erythro-(E)-3,5-dihydroxy-7-[1'-(3",5"-dimethylphenyl)-3'-methylnaphth-2'-yl]hept-6-enoate (Compound CCXL)

(a) 42 ml. of 1M. triethylborane/tetrahydrofuran (42 mmoles) is added dropwise to 11.6 g. (27 mmoles) of crude Compound CCXLVI (from Step 12) in 500 ml of dry tetrahydrofuran (distilled over sodium) stirred at 20°–25° C. under nitrogen, 200 ml. of air (at 760 mm. Hg. and 25° C.) is bubbled in, and the reaction mixture is stirred at 20°–25° C. for 1 hour and cooled to −78°–−69° C. 1.9 g. (50 mmoles) of sodium borohydride is added, and the reaction mixture is stirred at −78°–−69° C. for 16 hours under nitrogen. The reaction mixture is warmed to −20° C., and 150 ml. of 2N. hydrochloric acid is added dropwise with rapid agitation over a 15 minute period. Water is added, and the mixture is extracted with diethyl ether. The diethyl ether extract is dried over anhydrous sodium sulfate and evaporated to dryness at reduced pressure, and 50 ml. of isopropanol (reagent grade) is added. The mixture is heated in an oil bath for about 1 minute (100° C. bath temperature), allowed to cool and seeded with one crystal of the product (from a previous batch) and cooled in a refrigerator for 16 hours. The precipitate is collected by filtration, washed with cold isopropanol and dried under high vacuum to obtain the cyclic ethylboron ester (1.2 g.), m.p. 80°–81° C. A second crop (3.3 g.) and a third crop (1.07 g.) are also obtained.

(b) 4.49 g. (9.5 mmoles) of the cyclic ethylboron ester product of Part (a) of this step is stirred in 250 ml. of methanol (reagent grade) at 20°–25° C. for 5 hours. The reaction mixture is evaporated to dryness at reduced pressure, the residue is dissolved in diethyl ether, and the diethyl ether solution is washed with saturated sodium chloride solution, dried over anhydrous sodium sulfate and evaporated at reduced pressure to obtain the product as a light yellow oil (4.04 g.).

N.M.R. (CDCl$_3$): 1.30 (t, 3H (J=1.5 Hz.)), 1.45 (m, 2H), 2.35 (s, 6H), 2.42 (m, 2H), 2.50 (s, 3H), 3.65 (bm, 1H), 4.10 (bm, 1H), 4.15 (m, 1H), 4.20 (q, 2H (J=1.5 Hz.)), 4.35 (m, 1H), 5.45 (dd, 1H (J= 1.5 Hz and 2 Hz )), 6.50 (d, 1H (J=3.5 Hz.)), 6.85 (d, 2H), 7.0 (bs, 1H), 7.35 (m, 3H), 7.75 (m, 2H).

The product, the erythro racemate, contains a small amount of the corresponding threo racemate, the ratio of the erythro racemate to the threo racemate being about 18:1. The two racemates may be separated from each other by conventional means, and each may be resolved by conventional means. The erythro racemate yields the 3R,5S and 3S,5R enantiomers, and the threo racemate yields the 3R,5R and 3S,5S enantiomers

EXAMPLE 2

Sodium erythro-(E)-3,5-dihydroxy-7-[1'-(3",5"-dimethylphenyl)-3'-methylnaphth-2'-yl]hept-6-enoate

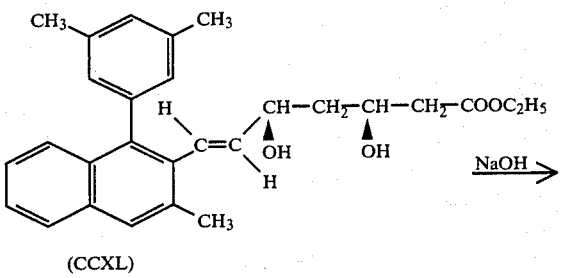

9.0 ml. of 1N. sodium hydroxide solution (9 mmoles) is added dropwise over a 15 minute period to 4.01 g. (9.3 mmoles) of Compound CCXL in 250 ml. of absolute ethanol stirred at 0°–5° C. The reaction mixture is stirred for 2 hours during the course of which the reaction mixture is allowed to warm to 20°–25° C. The reaction mixture is evaporated to dryness at reduced pressure, and the residue is dried under high vacuum for 2 hours and dissolved in chloroform (spectral grade). The chloroform solution is dried over anhydrous sodium sulfate, concentrated at reduced pressure to a volume of 50 ml. and, with cooling and stirring, anhydrous diethyl ether is added. The precipitate is collected by filtration, dried under nitrogen, washed with anhydrous diethyl ether and vacuum dried to obtain the product (3.49 g.), m.p.>230° C. (dec.)

N.M.R. (CDCl$_3$+CD$_3$OD): 1.3 (m, 2H), 2.25 (m, 2H), 2.35 (s, 6H), 2.52 (s, 3H), 4.01 (m, 1H), 4.28 (m, 1H), 5.45 (dd, 1H (J=1.25 Hz. and 2.0 Hz.)), 6.45 (d, 1H (J=3.5 Hz.)), 6.85 (d, 2H), 7.0 (s, 1H), 7.34 (m, 3H), 7.70 (m, 2H)

The product, the erythro racemate, contains a small amount of the corresponding threo racemate, the ratio of the erythro racemate to the threo racemate being about 18:1. The two racemates may be separated from each other by conventional means, and each may be resolved by conventional means. The erythro racemate yields the 3R,5S and 3S,5R enantiomers, and the threo racemate yields the 3R,5R and 3S,5S enantiomers.

EXAMPLE 3

Erythro-(E)-3,5-di
[1'-(3'',5''-dimethylphenyl)-3'-methylnaphth-2'-yl]hept-6-enoic acid

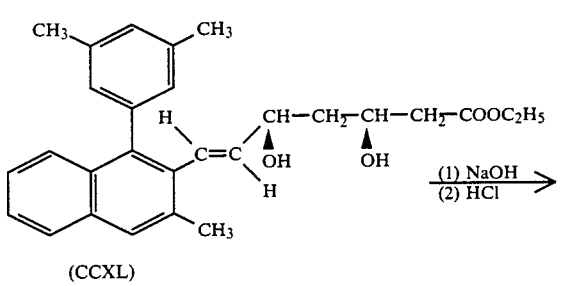

(CCXL)

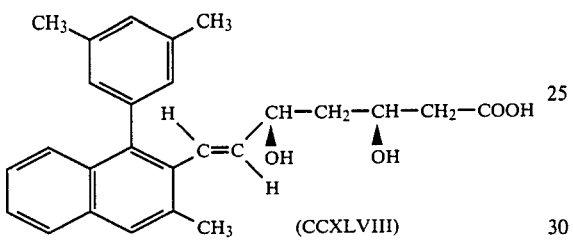

(CCXLVIII)

0.47 ml. of 1N. sodium hydroxide solution (0.47 mmole) is added dropwise over a 20 minute period to 201.4 mg. (0.47 mmole) of crude Compound CCXL (prepared from Compound CCXLVI substantially in accordance with the processes of Step 10 of Example 1, Step 14 of Example 5 and Step 13 of Example 11 of application Ser. No. 06/570,584) in 8 ml. of ethanol and 3 ml. of water stirred at 0°–5° C., and the reaction mixture is stirred for 1.5 hours at 0°–5° C. 0.5 ml. of 1N. hydrochloric acid (0.5 mmole) is added with stirring, water is added, and the mixture is extracted with ethyl acetate. The ethyl acetate extract is dried over anhydrous sodium sulfate and evaporated to dryness at reduced pressure to obtain the crude product.

The product, the erythro racemate, contains a small amount of the corresponding threo racemate, the ratio of the erythro racemate to the threo racemate being about 5.7:1. The two racemates may be separated from each other by conventional means and each may be resolved by conventional means. The erythro racemate yields the 3R,5S and 3S,5R enantiomers, and the threo racemate yields the 3R,5R and 3S,5S enantiomers.

Utilization in the process of this example of the product of Example 3 yields a mixture of the erythro and threo racemates wherein the ratio of the former to the latter is about 18:1.

EXAMPLE 4

(E)-Trans-6-(2'-[1''-(3''',5'''-dimethylphenyl)-3''-methylnaphth-2''-yl]ethenyl)-4-hydroxy-3,4,5,6-tetrahydro-2H-pyran-2-one

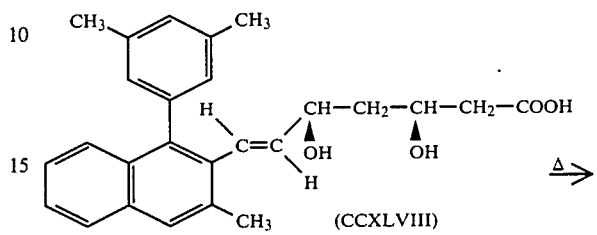

(CCXLVIII)

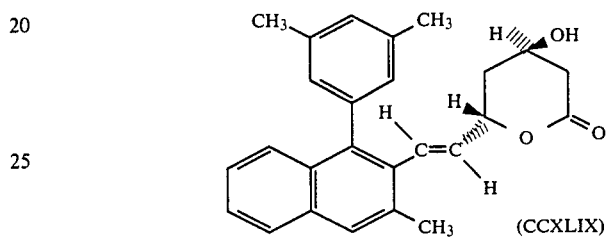

(CCXLIX)

The crude Compound CCXLVIII of Example 3 is refluxed in dry toluene for 4 hours. The reaction mixture is allowed to cool and is evaporated at reduced pressure to dryness, and the residue is chromatographed on silica gel preparative thin layer chromatography plates (1000 microns thick) utilizing 10% methanol/methylene chloride as the eluant. The desired material is eluted from the plates to obtain an oil which is vacuum dried to obtain the white crystalline product (136 mg.), m.p. 53°–56° C.

N.M.R. (CDCl$_3$): 1.65 (m, 2H), 1.73 (m, 1H), 2.39 (s, 6H), 2.52 (s, 3H), 2.65 (m, 2H), 4.02 (m, 1H), 5.12 (m, 1H), 5.45 (dd, 1H (J=1.25 Hz. and 2 Hz.)), 6.55 (d, 1H (J=3.25 Hz.)), 6.85 (m, 2H), 7.05 (s, 1H), 7.37 (m, 3H), 7.75 (m, 2H).

The product, the trans lactone racemate, contains a small amount of the corresponding cis lactone racemate, the ratio of the trans lactone to the cis lactone being about 5.7:1. The two racemic lactones may be separated from each other by conventional means, and each may be resolved by conventional means. The racemic trans lactone yields the 4R,6S and 4S,6R enantiomers and the racemic cis lactone yields the R,6R and 4S,6S enantiomers.

Utilization in the process of this example of a mixture of Compound CCXLVIII and the corresponding threo racemate wherein the ratio of the former to the latter is about 10:1 yields a mixture of the racemic trans and cis lactones wherein the ratio of the former to the latter is about 18:1.

EXAMPLE 5

Sodium erythro-(E)-3,5-dihydroxy-7-[1'-(3'',5''-dimethylphenyl)-3'-methylnaphth-2'-yl]hept-6-enoate

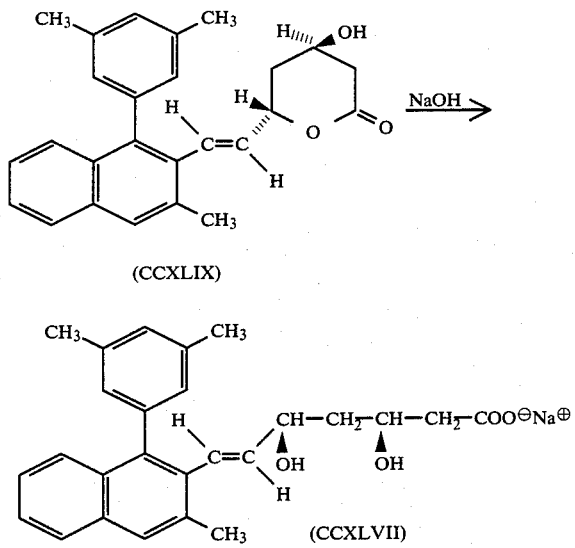

0.19 ml. of 1N. sodium hydroxide solution (0.19 mmole) is added dropwise to 82 mg. (0.21 mmole) of Compound CCXLIX (from Example 4) in 5.6 ml. of ethanol stirred at 20°-25° C. The reaction mixture is stirred at 20°-25° C. for 1.5 hours and evaporated to dryness at reduced pressure. The residue is dissolved in the minimum amount of methylene chloride, and diethyl ether is added dropwise. The precipitate is collected by filtration and vacuum dried to obtain the product (70.0 mg. (78.6%)), m.p. >230° C. (dec.)

The product, the erythro racemate, contains a small amount of the corresponding threo racemate, the ratio of the erythro racemate to the threo racemate being about 5.7:1. The two racemates may be separated from each other by conventional means, and each may be resolved by conventional means. The erythro racemate yields the 3R,5S and 3S,5R enantiomers, and the threo racemate yields the 3R,5R and 3S,5S enantiomers.

EXAMPLE A 4,4-Dimethyl-2-[1'-(3'',5''-dimethylphenyl)-3'-(1''-methylethyl)naphth-2'-yl]-2-oxazoline

Step 1

1,3-Dimethoxynaphthalene

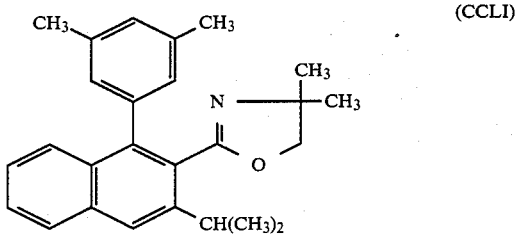

(CCLI)

Step 2

1,3-Dimethoxynaphthalene

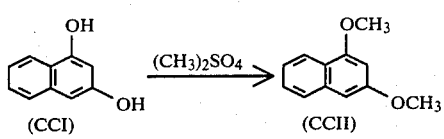

A solution of 32.1 g. (0.801 mole) of sodium hydroxide in 80.3 ml. of water and 96 g. (0.763 mole) of dimethyl sulfate are simultaneously added over a period of 30-45 minutes to g. (0.312 mole) of 1,3-dihydroxynaphthalene in 250 ml. of absolute ethanol stirred at −5°-0° C., the former being added slightly faster than the latter. The reaction mixture is allowed to gradually warm to 20°-25° C. with stirring over a 16 hour period. Most of the ethanol is evaporated at reduced pressure, water is added, and the mixture is extracted three times with methyl t-butyl ether. The extracts are combined, washed with 2N. aqueous sodium carbonate solution, dried over anhydrous sodium sulfate and evaporated to dryness at reduced pressure to obtain an oil. The oil is chromatographed on a Waters Prep-500 high pressure liquid chromatography apparatus having a silica gel column and utilizing 5% ethyl acetate/n-hexane as the eluant. The fractions containing the product are combined and evaporated at reduced pressure to obtain the product as a yellow oil (24.15 g.).

Step 2

1,3-Dimethoxy-2-naphthoic acid

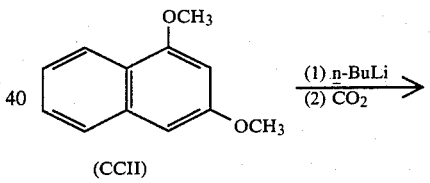

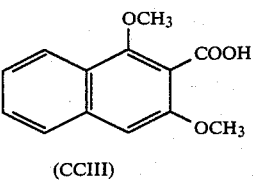

62 ml. of 1.55M. n-butyllithium/n-hexane (96 mmoles) is slowly added to 15.04 g. (80 mmoles) of 1,3-dimethoxynaphthalene in 250 ml. of anhydrous diethyl ether stirred at 0° C. under nitrogen. The reaction mixture is allowed to warm to 20°-25° C. and is stirred at this temperature for 20 hours, the reaction mixture being stirred under nitrogen throughout. Excess anhydrous carbon dioxide is bubbled in for 30 minutes. The reaction mixture is stirred at 20°-25° C. for 4 hours, quenched with water and extracted thoroughly with ethyl acetate. The alkaline aqueous phase is acidified with 2N. hydrochloric acid (to a pH of 1-2) and extracted with ethyl acetate. This ethyl acetate extract is dried over anhydrous sodium sulfate and evaporated to dryness. The residue is dried under high vacuum to obtain the product (18.3 g.), m.p. 119°-123° C.

Step 3

1,3-Dimethoxy-2-naphthoyl chloride

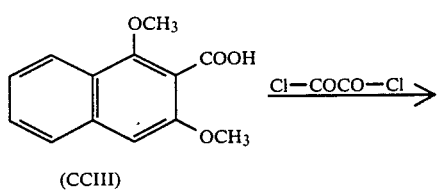

(CCIII)

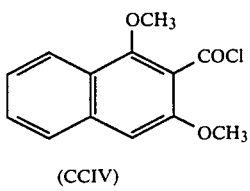

(CCIV)

The product is prepared from 9.28 g. (40 mmoles) of 1,3-dimethoxy-2-naphthoic acid and 10.15 g. (80 mmoles) of oxalyl chloride by the process of Step 3 of Example 1.

Step 4

1,3-Dimethoxy-2-naphthoic acid N-1,1-dimethyl-2-hydroxyethylamide

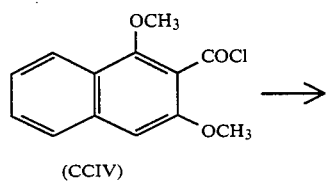

(CCIV)

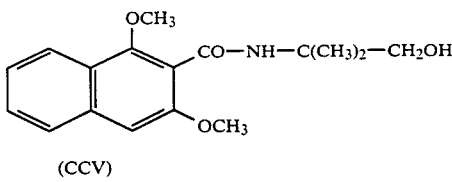

(CCV)

The crude product (12 0 g.) is obtained as a yellow foam from the crude product of Step 3 of this example and 7.12 g. (80 mmoles) of 2-amino-2-methyl-1-propanol substantially according to the process of Step 4 of Example 1.

Steps 5 and 6

2-(1',3'-dimethoxynaphth-2'-yl)-4,4-dimethyl-2-oxazoline and its hydrochloride salt

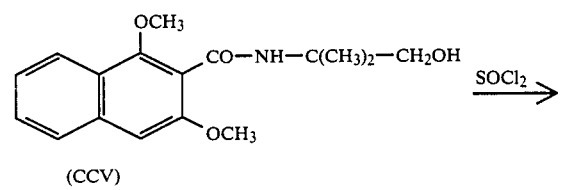

(CCV)

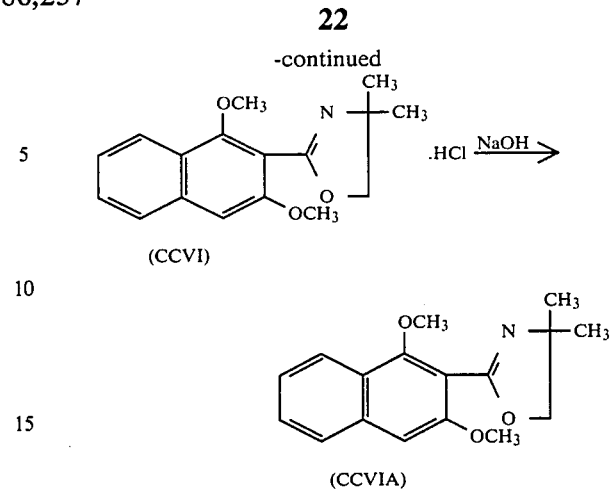

(CCVI)

(CCVIA)

The crude product (1.7 g.) is obtained from 3.03 g. (10 mmoles) of Compound CCV, 3.6 g. (30 mmoles) of thionyl chloride and 10 ml. of 20% aqueous sodium hydroxide solution substantially according to the processes of Steps 5 and 6 of Example 1, the principal differences being that the reaction times for Steps 5 and 6 are about 60 hours and 2 hours, respectively, and Step 6 is run in 10% sodium hydroxide solution. The product is purified by preparative thin layer chromatography on silica gel plates utilizing 2% methanol/methylene chloride as the solvent and ethyl acetate to elute the purified product from the plates. The product is obtained as a yellow gum (1.33 g.).

Step 7

4,4-Dimethyl-2[1'-(3",5"-dimethylphenyl)-3'-methoxynaphth-2'-yl]-2-oxazoline

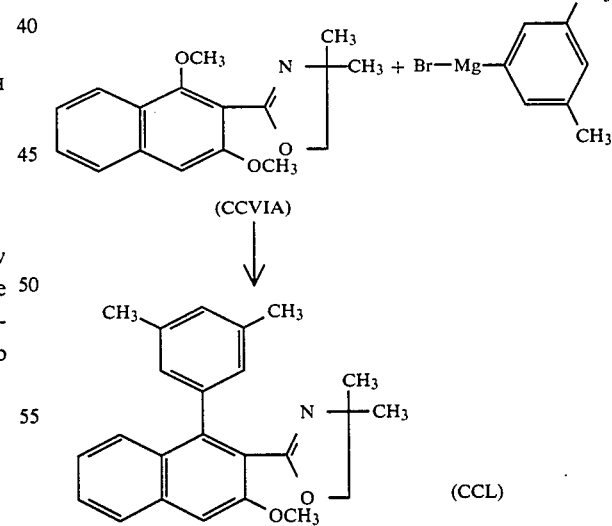

(CCVIA)

(CCL)

18 ml. of a 1M. solution of 3,5-dimethylphenylmagnesium bromide (18 mmoles) in dry tetrahydrofuran (prepared as described in Step 7 of Example 1) is slowly added to 4.25 g. (14.9 mmoles) of Compound CCVIA in 80 ml. of dry tetrahydrofuran (distilled from sodium) stirred at 20°-25° C. under nitrogen, and the reaction mixture is stirred at 20°-25° C. under nitrogen for 16 hours and quenched with ice and saturated. aqueous ammonium chloride solution. The mixture is extracted with ethyl acetate, and the ethyl acetate extract is dried over anhydrous soudium sulfate and evaporated to a small volume at reduced pressure to obtain the product. The product is collected by filtration, washed with a small amount of diethyl ether, washed with a small amount of petroleum ether and dried under high vancuum.

Step 8

4,4-Dimethyl-2[1'-(3",5"-dimethylphenyl)-3'(1"-methylethyl)naphth-2'-yl]2-oxazoline

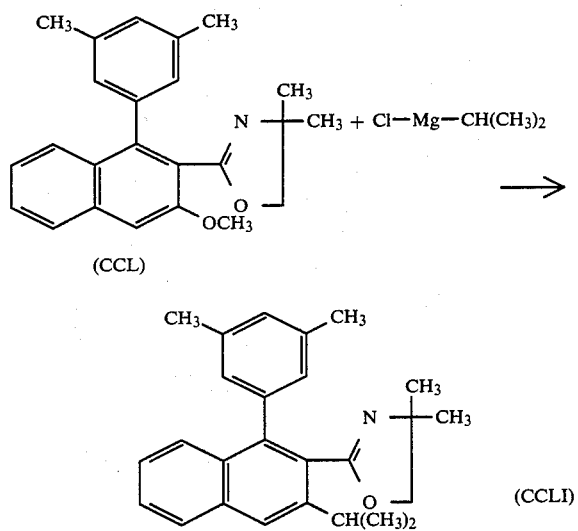

13 25 ml. of 2M. isopropylmagnesium chloride/diethyl ether (26.5 mmoles) is slowly added to 1.59 g. (4.41 mmoles) of Compound CCL in 90 ml of dry tetrahydrofuran (distilled from sodium) and 22 ml. of dry toluene (dried over molecular sieves) stirred at 20°-25° C., the reaction mixture is stirred at 20°-25° C. for 30 minutes and at 70°-80° C. for 18 hours, an additional 13.25 ml of 2M. isopropylmagnesium chloride/diethyl ether (26.5 mmoles) is added, and tho reaction mixture is stirred at 70°-80° C. for an additional 20 hours, the reaction mixture being maintained under nitrogen throughout. The reaction mixture is quenched with ice and saturated aqueous ammonium chloride solution and extracted with ethyl acetate. The ethyl acetate extract is dried over anhydrous sodium sulfate and evaporated to dryness at reduced pressure. The residue is dissolved in methylene chloride, and the solution is dried over anhydrous sodium sulfate and evaporated to dryness at reduced pressure. The obtained gum is dissolved in about 10 ml. of methylene chloride, a small amount of charcoal is added, and the solution is filtered through a silica gel column utilizing methylene chloride as the eluant. The fractions containing the product as determined by thin layer chromatography are combined and evaporated to dryness at reduced pressure to obtain the product.

Steps 3-6 of this example are described in further detail in application Ser. No. 06/570,584.

Throughout the examples, the term "reduced pressure" denotes aspirator pressure. Where no solvent is specified in connection with a solution, the solvent is water, and all solvent mixtures are by volume. When a reaction is carried out under nitrogen, dry nitrogen is used to maintain anhydrous conditions.

All nuclear magnetic resonance spectra were taken at ambient temperature on a 200 MHz. spectrometer. All chemical shifts are given in p.p.m. ($\delta$) relative to tetramethylsilane, and where a single $\delta$ value is given for anything other than a sharp singlet, it is its center point. In the N.M.R.

bm=broad multiplet
bs=broad singlet
d=doublet
dd=doublet of a doublet
m=multiplet
q=quartet
s=singlet
t=triplet The compound of Example 2 (wherein Z is a group of Formula a wherein $R_7$ is sodium) may be converted into the corresponding compounds wherein $R_7$ is a different cation M, particularly M', by the processes set forth in the specification.

Each of the compounds of Examples 1-5 (including each of the possible optical isomers) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

What is claimed is;

1. A compound of the formula

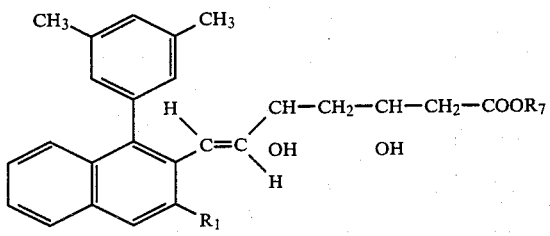

wherein
$R_1$ is $C_{1-3}$alkyl, and
$R_7$ is hydrogen, $R_8$ or M,
wherein
$R_8$ is a physiologically acceptable and hydrolyzable ester group, and
M is a cation.

2. A compound according to claim 1 wherein M is a pharmaceutically acceptable cation.

3. A compound according to claim 2 wherein $R_7$ is hydrogen, $C_{1-3}$alkyl or M, wherein M is a pharmaceutically acceptable cation.

4. A compound according to claim 3 wherein $R_7$ is a pharmaceutically acceptable cation.

5. A compound according to claim 4 wherein $R_7$ is sodium.

6. A compound according to claim 4 wherein $R_1$ is methyl or isopropyl.

7. A compound according to claim 6 wherein $R_7$ is sodium.

8. The compound according to claim 7 having the formula

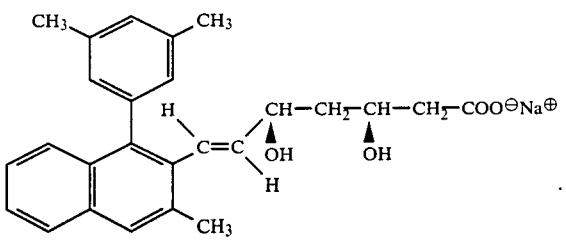

9. The compound according to claim 3 having the formula

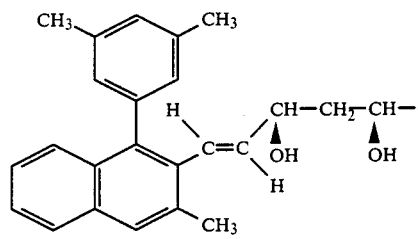

10. A pharmaceutical composition comprising an effective amount of a compound according to claim 2 and a harmaceutically acceptable carrier, said effective amount being an amount sufficient to inhibit cholesterol biosynthesis in a mammal.

11. A pharmaceutical composition according to claim 10 comprising an effective amount of the compound of the formula

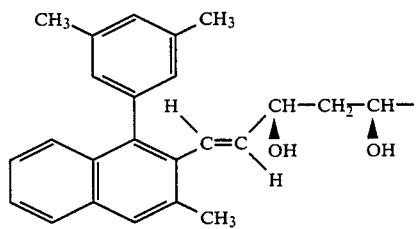

said effective amount being an amount sufficient to inhibit cholesterol biosynthesis in a mammal.

12. A method of inhibiting cholesterol biosynthesis comprising administering to a mammal in need of such treatment an effective amount of a compound according to claim 2, said effective amount being an amount effective for inhibiterol biosynthesis.

13. A method of treating atherosclerosis comprising administering to a mammal in need of such treatment an effective amount of a compound according to claim 2, said effective amount being an amount effective for the treatment of atherosclerosis.

14. A method of treating atherosclerosis according to claim 13 comprising administering to a mammal in need of such treatment an effective amount of a compound of the formula

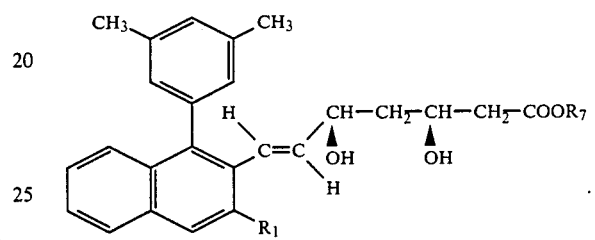

15. A method of treating atherosclerosis according to claim 14 comprising administering to a mammal in need of such treatment an effective amount of the compound of the formula

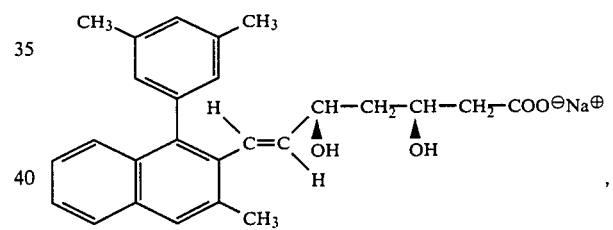

said effective amount being an amount effective for the treatment of atherosclerosis.

* * * * *